United States Patent
Romeo et al.

(10) Patent No.: US 6,224,857 B1
(45) Date of Patent: May 1, 2001

(54) PHARMACEUTICAL PREPARATIONS COMPRISED OF SALTS OF HYALURONIC ACID WITH LOCAL ANAESTHETICS

(75) Inventors: Aurelio Romeo; Bruno Silvestrini, both of Rome; Gunter Kirschner, Abano Terme, all of (IT)

(73) Assignee: Fidia, S.p.A., Abano Terme (IT)

( * ) Notice: Subject to any disclaimer, the term of this patent is extended or adjusted under 35 U.S.C. 154(b) by 0 days.

(21) Appl. No.: 09/284,668

(22) PCT Filed: Oct. 17, 1997

(86) PCT No.: PCT/IB97/01288
§ 371 Date: Jul. 19, 1999
§ 102(e) Date: Jul. 19, 1999

(87) PCT Pub. No.: WO98/17285
PCT Pub. Date: Apr. 30, 1998

(30) Foreign Application Priority Data

Oct. 17, 1996 (IT) .............................................. PD96A0254

(51) Int. Cl.$^7$ ................................ A61K 31/74; A61K 9/70
(52) U.S. Cl. ......................................... 424/78.04; 424/443
(58) Field of Search .................................. 424/443, 78.04

(56) References Cited

U.S. PATENT DOCUMENTS 5,942,241 * 8/1999 Chasin .

FOREIGN PATENT DOCUMENTS

| 0216453B1 | 4/1987 | (EP) . |
| WO9218543 | 10/1992 | (WO) . |

* cited by examiner

*Primary Examiner*—Carlos A. Azpuru
(74) *Attorney, Agent, or Firm*—Birch, Stewart, Kolasch & Birch, LLP; Leonard R. Svensson

(57) ABSTRACT

Pharmaceutical preparations are described, comprised of salts of hyaluronic acid with a basic anesthetic containing aliphatics and/or amino groups, particularly salts with benzydamine or bupivacaine.

12 Claims, No Drawings

PHARMACEUTICAL PREPARATIONS COMPRISED OF SALTS OF HYALURONIC ACID WITH LOCAL ANAESTHETICS

This application is the national phase under 35 U.S.C. §371 of prior PCT International Application No. PCT/IB97/01288 which has an international filing date of Oct. 17, 1997 which designated the United States of America, the entire contents of which are hereby incorporated by reference.

FIELD OF THE INVENTION

The present invention relates to the use of new pharmaceutical preparations in the field of local anaesthetics and, more precisely, preparations consisting of a stoichiometrically neutral salt of a hyaluronic acid with a basic anaesthetic with local action containing aliphatic and/or aromatic amino groups with an aliquot of the carboxy groups of hyaluronic acid possibly salified with an alkaline or alkaline earth metal.

The invention also concerns some new compositions of the aforesaid type which, thanks to their specific pharmaceutical properties as described hereafter, are suitable for use as infiltrations and injections as well as for surface use.

FIELD OF THE INVENTION

European patent No 0197718 B1 granted on Dec. 15, 1993 describes the advantageous use of hyaluronic acid and molecular fractions thereof as vehicles for medicinal substances for topical use and demonstrates that associations of hyaluronic acid with known drugs in various fields of medicine give better effects than the same drugs administered on their own. That patent emphasises above all a greater degree of bioavailability than that obtained with the pharmaceutical formulations used in the past, and this advantage is illustrated especially in the ophthalmic field, where marked compatibility with the corneal epithelium was observed, with subsequent excellent tolerability with no sensitization effects, with the formation of homogeneous and stable films which are perfectly transparent, have excellent adhesive properties and guarantee prolonged bioavailability of the drug.

The above patent discusses the importance of said perfected bioavailability in the veterinary field with regard to the administration of chemotherapeutics. The patent also lists miotic, anti-inflammatory, wound healing and antimicrobial effects for ophthalmic use in the fields of both veterinary and human medicine.

DETAILED DESCRIPTION OF THE INVENTION

It has now been discovered that the use of local anaesthetics, and more precisely basic organic anaesthetics containing amino groups, if used in the form of their stoichiometrically neutral salts with hyaluronic acid, or stoichiometrically neutral salts of hyaluronic acid with such anaesthetics, resulting from partial salification of the hyaluronic acid with said aminic substances and from the salification of the remaining carboxy groups of the acid with inorganic bases deriving from alkaline or alkaline earth metals, not only offers the advantages of enhanced bioavailability and excellent tolerability, but also induce an exceptional increase in the anaesthetic effect. This result is of great importance in the ophthalinological field but can be used in other fields as well. It constitutes a specific technical effect over and above the benefits reported in the aforesaid previous patent.

In the context of the present invention, the term "hyaluronic acid" indicates a purified hyaluronic acid such as those already on the market or described in the literature or in patents such as those obtained by extraction from animal or fermentation sources, or of biotechnological origin, or molecular fractions of hyaluronic acids, likewise purified, such as those described in European patent No. 0138572 (describing commercial products known as Hyalastine and Hyalectin) or hyaluronic acids with higher molecular weights such as the fraction known as Hyaloftil, described in EP 0535200 A1, or other products available on the market. Besides the hyaluronic acid described above, its partial esters obtained according to the procedure described in EP 0216453 B1 can also be used.

The local anaesthetics for use in the preparation of salts with hyaluronic acid according to the present invention are essentially those reported in the literature and/or found on the market or used for clinical purposes, and which contain aliphatic and/or aromatic amino groups (with between 12 and 30 carbon atoms) which can be salified with an acid. While the salts of hyaluronic acid with lidocaine, dibucaine and benzocaine are known, as they are described in the aforesaid European patent No. 0197718 B1, the salts of hyaluronic acid with the following aminic-type local anaesthetics to be used according to the invention are new and constitute a particular object of the invention: tetracaine, amylocaine, bucricaine, bupivacaine, butacaine sulfate, butanilicaine, butoxycaine, carticaine, chloroprocaine, clibucaine, chlormecaine, cyclomethycaine, dimethisoquin hydrochloride, diperodon, diclocaine, ethyl p-piperidine acetylamine benzoate, ethidocaine, hexylcaine, phenacaine, fomocaine, hydroxyprocaine, hydroxytetracaine, ketocaine, oxethazaine, oxybuprocaine, paretoxycaine, piperocaine, piridocaine, pyrrocaine, pramoxine, prilocaine, procaine, propanocaine, propipocaine, propoxycaine, proxymetacaine, ropivacaine, tolycaine, trimecaine, vadocaine and, especial, benzydamine, a drug characterized by anti-inflammatory and local anaesthetic properties.

The salts of hyaluronic acid with a strong anaesthetic effect according to the present invention are above all stoichiometrically neutral salts with the abovesaid aminic bases, that is, the total salts of the polysaccharide with aminic bases. In the partial salts of the polysaccharide with said aminic bases, the degree of salification may vary within an ample range, for example between 10% and 90%, preferably between 20% and 80%, and especially between 50% and 75%, with the remaining carboxy groups of the polysaccharide are salified with one of the abovesaid ions of an alkaline or alkaline earth metal.

A preferred object of the invention is represented by the total and partial salts, as described above, of benzydamine with a hyaluronic acid. It has been observed that salts of this kind not only present a far more pronounced and longer-lasting anaesthetic effect than benzydamine or the hydrochloride thereof but also enhance the anti-inflammatory effect and, surprisingly reduce the irritating action, thus widening the gap between active and irritant concentrations or doses. Indeed, it is known that, as an anaesthetic or anti-inflammatory agent, benzydamine presents some disadvantages, such as the brevity of its topical action, as the drug quickly passes from the application site into the system, and the onset of an irritant action, which occurs at doses not far removed from those required for the desired effects.

It has further been found according to the invention that the activity of the hyaluronic acid salts with anaesthetics can vary depending upon the molecular weight of the hyaluronic acid. For one of the preferred anaesthetics, benzydamine, it was found that the product has the most improved characteristics when salified with a low molecular weight fraction of hyaluronic acid. For another preferred anaesthetic, bupivacaine, it was found that the product has the most improved characteristics when salified with a high molecular weight fraction of hyaluronic acid. It has also been found that of the alkaline and alkaline earth metals, sodium salts are the preferred monovalent salts, and calcium salts are the preferred bivalent salts.

It follows that the new benzydamine salts of the present invention, besides their advantageous application in ophthalmology, like the other anaesthetic bases mentioned previously, have proved to be new drugs with a very wide field of application, for example in inflammatory processes in the mouth or airways such as stomatitis of various origin, tonsillitis or tracheitis, in mucositis caused by radio- or chemotherapy, by sub or diagnostic intubation, such as bronchoscopy, in dental and gingival disorders in general, including teething trouble in babies, in rhinitis, in inflammatory processes affecting the auditory canal, in conjunctivitis of various origin, in proctological conditions, in traumatic and degenerative-inflammatory processes in the joints, in vulvovaginitis and urethritis of various kinds, including those caused by radio- and chemotherapy, surgical operations, diagnostic manoeuvres, childbirth and, in general, any inflammatory disorder of any kind.

The technical effect of the new hyaluronic acid salts according to the present invention can be demonstrated by the following experimental results relating to its greater anaesthetic action compared to that of the anaesthetic component used on its own (Tables 1–6), in dry inflammation of the eye in rabbit. Benzydamine salts too show a reduction in the substance's irritant action (Tab 7).

BIOLOGICAL TESTS

A. Assessement of the Anaesthetic Effect on Rabbit Cornea of Hyaluronic Acid Salts with Local Anaesthetics Methods Corneal Anaesthesia Corneal anaesthesia was assessed by the method of Camougis and Tankman (Camougis et al. (1971), "Methods in Pharmacology", Vol. 1, A. Schwartz Ed., Appleton-Century-Crofts, New York p. 1) by measuring the blinking reflex in rabbit. Fifty ml of solution was instilled in the conjunctival sac. The blinking reflex, tested with a bristle, was measured before instillation and then every 5–10 minutes until one hour after treatment. At each test time the degree of anaesthesia was expressed by means of a score of up to 10 given by the number of stimulations before the eye-blink reflex was obtained. The overall anaesthetic effect for each compound was then quantified by the area under curve (AUC) of the degree of anaesthesia over time.

Results

As indicated by the results in Table 1, the hyaluronate salts of lidocaine, bupivacaine and benzydamine present greater local activity than their respective hydrochloride salts. As can be observed the effect of increasing the action of the anaesthetics varies according to the alkaline or alkaline/earth ion; the presence of calcium, unlike sodium, selectively favours lidocaine rather than bupivacaine or benzydamine.

TABLE 1

Anaesthetic effect in rabbit eye by hyaluronate of lidocaine, bupivacaine, benzydamine (FID 60.20XX) and their respective hydrochloride salts.

| Compound* | Dose§ (concentration) | Anaesthesia (AUC)$ |
|---|---|---|
| Lidocaine HCl | 1% | 100 |
| FID 60.2070 | 1% | 167 |
| (100% lidocaine) | | |
| FID 60.2071 | 1% | 244 |
| (50% lidocaine - 50% Na) | | |
| FID 60.2072 | 1% | 222 |
| (50% lidocaine - 50% Ca) | | |
| FID 60.2088 | 1% | 200 |
| (50% lidocaine - 50% K) | | |
| Bupivacaine HCl | 0.125% | 100 |
| FID 60.2082 | 0.125% | 166 |
| (100% bupivacaine) | | |
| FID 60.2083 | 0.125% | 205 |
| (50% bupivacaine - 50% Na) | | |
| FID 60.2084 | 0.125% | 112 |
| (50% bupivacaine - 50% Ca) | | |
| Benzydamine Hcl | 0.125% | 100 |
| FID 60.2096 | 0.125% | 153 |
| (50% benzydamine - 50% Na) | | |
| FID 60.2097 | 0.125% | 110 |
| (50% benzydamine - 50% Ca) | | |

*For the hyaluronate salts, the % of active principle and that of alkaline or alkaline earth ion are shown;
§the doses refer in all cases to the active principle as a hydrochloride salt;
$AUC measurements of the anaesthetic effect are calculated by taking the reference active principle value as 100.

This ion selectivity has proved to also depend upon the molecular weight of the hyaluronic acid used. As can be seen from Table 2, the ion selectivity only exists in low-molecular-weight hyaluronic acid, specifically molecular weight range of 50–350 kDa (derivatives FID 602(XX), and not in high-molecular-weight hyaluronic acid, molecular weight range of 500–730 Kda and 750–1200 (derivatives FID 61.2OXX and FID 62.20XX, respectively).

TABLE 2

Anaesthetic effect in rabbit eye by hyaluronate salts of bupivacaine, according to the molecular weight of the hyaluronic acid of the alkaline or alkaline earth counterion.

| Compound* | Dose$ | Anaesthesia (AUC)$ |
|---|---|---|
| FID 60.2082 | 0.125% | 100 |
| (100% bupivacaine) | | |
| FID 60.2083 | 0.125% | 123 |
| (50% bupivacaine - 50% Na) | | |
| FID 60.2084 | 0.125% | 84 |
| (50% bupivacaine - 50% Ca) | | |
| FID 61.2082 | 0.125% | 100 |
| (100% bupivacaine) | | |
| FID 61.2083 | 0.125% | 96 |
| (50% bupivacaine - 50% Na) | | |
| FID 61.2084 | 0.125% | 104 |
| (50% bupivacaine - 50% Ca) | | |
| FID 62.2082 | 0.125% | 100 |
| (100% bupivacaine) | | |
| FID 62.2083 | 0.125% | 116 |
| (50% bupivacaine - 50% Na) | | |
| FID 62.2084 | 0.125% | 110 |
| (50% bupivacaine - 50% Ca) | | |

*For the hyaluronate salts, the % of active principle and that of alkaline or alkaline earth ion are shown;
§the doses refer in all cases to the active principle as a hydrochloride salt;
$AUC measurements of the anaesthetic effect are calculated by taking the reference product value as 100.

Moreover, as can be seen from Table 3, the degree of activity depends on the molecular weight of the hyaluronic acid used.

TABLE 3

Anaesthetic effect on rabbit eye by hyaluronate salts of bupivacaine according to the molecular weight of the hyaluronic acid.

| Compound* | Dose§ | Anaesthesia (AUC)$ |
|---|---|---|
| Bupivacaine Hcl | 0.125% | 100 |
| FID 60.2083 (50% bupivacaine - 50% Ca) | 0.125% | 123 |
| FID 61.2083 (50% bupivacaine - 50% Na) | 0.125% | 169 |
| FID 62.2083 (50% bupivacaine - 50% Na) | 0.125% | 168 |
| Bupivacaine Hcl | 0.125% | 100 |
| FID 60.2084 (50% bupivacaine - 50% Ca) | 0.125% | 102 |
| FID 61.2084 (50% bupivacaine - 50% Ca) | 0.125% | 180 |
| FID 62.2084 (50% bupivacaine - 50% Ca) | 0.125% | 205 |

*For the hyaluronate salts, the % of active principle and that of alkaline or alkaline earth ion are shown;
§the doses refer in all cases to the active principle as a hydrochloride salt;
$AUC measurements of the anaesthetic effect are calculated by taking the reference product value as 100.

Among monovalent alkaline salts, the most active derivatives are obtained by salification with sodium, as can be seen in Table 4, where derivatives of lidocaine with hyaluronic acid having a molecular weight range between 60 and 350 Kda are reported.

TABLE 4

Anaesthetic effect on rabbit eye by hyaluronate salts of lidocaine and its alkaline salts.

| Compound* | Dose§ | Anaesthesia (AUC)$ |
|---|---|---|
| Lidocaine Hcl | 0.125% | 100 |
| FID 60.2087 (50% lidocaine - 50% Li) | 0.125% | 197 |
| FID 61.2083 (50% lidocaine - 50% Na) | 0.125% | 244 |
| FID 62.2083 (50% lidocaine - 50% K) | 0.125% | 173 |

*For the hyaluronate salts, the % of active principle and that of alkaline ion are shown;
§the doses refer in all cases to the active principle as a hydrochloride salt;
$AUC measurements of the anaesthetic effect are calculated by taking the reference product value as 100.

The degree of salification influences the biological activity of the derivatives, as can be seen in Table 5, where partial salts with bupivacaine and sodium of hyaluronic acid having a molecular weight range between 500 and 730 Kda are reported in comparison to the hydrochloride and the total salt; and in Table 6, where partial salts with benzydamine and sodium of hyaluronic acid having a molecular weight range between 50 and 350 Kda are reported in comparison to the hydrochloride.

TABLE 5

Anaesthetic effect on rabbit eye by hyaluronate salts of bupivacaine according to the degree of salification.

| Compound* | Dose§ | Anaesthesia (AUC)$ |
|---|---|---|
| Bupivacaine HCl | 0.125% | 100 |
| FID 61.2110 (50% bupivacaine - 74% Na) | 0.125% | 171 |
| FID 61.2083 (50% bupivacaine - 50% Na) | 0.125% | 169 |

TABLE 5-continued

Anaesthetic effect on rabbit eye by hyaluronate salts of bupivacaine according to the degree of salification.

| Compound* | Dose§ | Anaesthesia (AUC)$ |
|---|---|---|
| FID 61.2109 (75% bupivacaine - 25% Na) | 0.125% | 221 |
| FID 61.2082 (100% bupivacaine) | 0.125% | 314 |

*For the hyaluronate salts, the % of active principle and that of alkaline ion are shown;
§the doses refer in all cases to the active principle as a hydrochloride salt;
$AUC measurements of the anaesthetic effect are calculated by taking the reference product value as 100.

TABLE 6

Anaesthetic effect on rabbit eye by hyaluronate salts of benzydamine according to the degree of salification.

| Compound* | Dose§ | Anaesthesia (AUC)$ |
|---|---|---|
| Benzydamine HCl | 0.125% | 100 |
| FID 60.2102 (10% benzydamine - 90% Na) | 0.125% | 143 |
| FID 60.2101 (25% benzydamine - 75% Na) | 0.125% | 148 |
| FID 60.2096 (50% benzydamine - 50% Na) | 0.125% | 153 |
| FID 60.2108 (75% benzydamine - 25% Na) | 0.125% | 197 |
| FID 60.2107 (90% benzydamine - 10% Na) | 0.125% | 181 |

*For the hyaluronate salts, the % of active principle and that of alkaline ion are shown;
§the doses refer in all cases to the active principle as a hydrochloride salt;
$AUC measurements of the anaesthetic effect are calculated by taking the reference product value as 100.

B. Assessment of the Reduction of the Irritant Effect of Benzydamine Salts in Rat Paw Methods Iritation 0.1 ml of each of the test solutions (1%, w/v, in hydrochloride salt) was injection into the hind paw of rat. The paw volume was measured with a plethismometer before injection and then 30–60–120–240–480 minutes after. The oedema and consequent irritant effect were measured on the basis of the increase in the volume of the paw. The irritant effect is expressed by the sum of the increase in volume at the various measuring times.

Results

The hyaluronate salt proved to be less irritating than the hydrochloride salt, as indicated by its lesser oedema-forming effect (Table 7).

TABLE 7

Irritant effect of benzydamine Hcl and FID 60.2108 in rat paw.

| Compound | No. | Oedema mean cumulative volume (ml) |
|---|---|---|
| Benzydamine Hcl mg | 20 | 529 |
| FID 60.2108 1 mg (75% benzydamine 25% Na) | 20 | 389 |

In the case of FXD 60.2108, the % of active principle and that of Na ion are indicated.
All doses refer to the active principle as a hydrochloride salt.

Methods of Preparation

The types of hyaluronic acid and basic anaesthetics to be used as staring products are already known and can be prepared by the known processes, as described hereafter. The invention can be illustrated by the following Examples:

Example 1

The hyaluronic acid sodium salt (molecular weight 50–350 Kda) is solubilized in water to a concentration of 16 mg/ml. A column is filled with acid resin Bio-Rad AG50W-X8, pretreated with Hcl 1N, using a glass column fitted with a jacket inside which there is a flow of fluid at 4° C.; 5 ml of resin in acid form are loaded in the column and washed with water to a neutral Ph. At this point the solution of hyaluronic acid sodium salt is passed through the resin, and the resulting solution is collected in a container with a thermostat set at 4° C.

The flow in the column is regulated by a peristaltic pump fitted to the outlet of the column. Once all the solution has passed through the column, the resin is washed with water to minimize any loss of product, and the products of these washes are added to the hyaluronic acid solution, thus obtaining a final solution with a concentration of 11.8 mg/ml, expressed as hyaluronic acid.

Example 2

The hyaluronic acid sodium salt (molecular weight 500–730 Kda) is solubilized in water to a concentration of 6.0 mg/ml. A column is filled with acid resin Bio-Rad AG50W-X8, pretreated with HCl 1N, using a glass column fitted with a jacket, inside which fluid flows at a temperature of 4° C.; 5 ml of resin in acid form are loaded in the column and washed with water until a neutral pH is reached. At this point the hyaluronic acid sodium salt solution is passed through the resin, collecting the resulting solution in a container set at temperature of 4° C.

The fluid in the column is regulated by a peristaltic pump fitted onto the outlet of the column. Once the solution has passed through the column, the resin is washed with water to minimize any loss of product, and the product of these washes is added to the hyaluronic acid solution, thus obtaining a final solution wit a concentration of 3.78 mg/ml, expressed as hyaluronic acid.

Example 3

Hyaluronic acid sodium salt (molecular weight 750–1200 kDa) is solubilized in water to a concentration of 3.0 mg/ml. A column is filled with acid resin. Bio-Rad AG50W-X8 pretreated with HCl 1N, using a glass column fitted with a jacket through which fluid flows at a temperature of 4° C.; 5 ml of resin in acid form is loaded in the column and washed with water to a neutral pH. At this point, the hyaluronic acid sodium salt is passed through the resin, collecting the resulting solution in a container with a thermostat set at 4° C.

The flow through the column is regulated by a peristaltic pump fitted onto the outlet of the column. Once the solution has passed through the column, the resin is washed with water to minimize any loss of product, then adding the product of the washes to the hyaluronic acid solution, thus obtaining a final solution with a concentration of 2.36 mg/ml, expressed as hyaluronic acid.

Example 4

80 ml of an aqueous solution of hyaluronic acid, prepared as described in Example 1, at a concentration of 11.8 mg/ml, is placed in a 100 ml flask. The solution is shaken in a thermostat bath set at 4° C. 0.77 g of benzydamine base is diluted with 10 ml of tert-butanol and the solution is slowly added drop by drop to the hyaluronic acid solution: a white precipitate is formed which disappears within a few hours. The container used to weigh the benzydamine is washed with two 5 ml aliquots of tert-butanol which are then added to the hyaluronic acid solution. The salification reaction is considered to be complete when there is no more suspended precipitate in the solution.

At this point the solution is filtered on a Gooch 4 filter, subdivided into yellow lass bottles and freeze-dried. The stoichiometrically neutral salt of hyaluronic acid with benzydamine is thus obtained.

The benzydamine to use as starting product can be prepared as of follows: 3.0 g of benzydamine hydrochloride are solubilized in water at a concentration of 50 mg/ml. An equimolar quantity of NaOH 1N is added, plus 5% excess, so as to give the aqueous solution a pH of between 10 and 11.

In these conditions the benzydamine base is released and separates from the water as an oil. It is partitioned with ethyl ether (two 50 ml partitionings) to extract the base completely. The ether phases are pooled dehydrated with anhydrous sodium sulfate, then evaporated to dryness and the oily residue is vacuum-dried. The product thus obtained is tested for purity on TLC (eluent: ethyl acetate/methanol 70:30; Rf=0.14).

Example 5

80 ml of an aqueous solution of hyaluronic acid, prepared as in Example 1, at a concentration of 11.8 mg/ml is placed in a 100 ml flask. The solution is shaken in a thermostat bath set at 4° C. 0.58 g of benzydamine base diluted with 10 ml of tert-butanol and the solution is slowly added drop by drop to the hyaluronic acid solution: a white precipitate is formed which disappears within a few hours. The container used to weigh the benzydamine is washed with two 5 ml aliquots of tert-butanol which are then added to the hyaluronic acid solution. A few hours later, when there is no more suspended precipitate in the solution, 0.62 ml of NaOH 1N is added and shaken for another 30 minutes.

At this point the solution is filtered through a Gooch G4 filter, subdivided into yellow glass bottles and freeze-dried. The neutral salt partially salified (75%) with benzydamine and partially salified (25%) with sodium.

The benzydamine to be used as starting product can be prepared as described in Example 4.

Example 6

80 ml of an aqueous solution of hyaluronic acid, prepared as described in Example 1, at a concentration of 11.8 mg/ml, is placed in a 100 ml flask. The solution is shaken in a thermostat bath set at 4° C. 0.39 g of benzydamine base is diluted with 10 ml of tert-butanol and the solution is slowly added drop by drop into the hyaluronic acid solution. A white precipitate is formed which disappears within a few hours. The container used to weigh the benzydamine is washed with two 5 ml aliquots of tert-butanol which are then added to the hyaluronic acid solution. Some hours later, when there is no more suspended precipitate present in the solution, 1.25 ml of NaOH 1N are slowly added and the mixture is shaken for another 30 minutes.

At this point the solution is filtered through a Gooch G4 filter, subdivided into yellow glass bottles and freeze-dried.

The neutral salt, partially salified (50%) with benzydamine and partially salified (50%) with sodium is thus obtained.

The benzydamine used as starting product can be prepared as described in Example 4.

Example 7

80 ml of an aqueous solution of hyaluronic acid, prepared as described in Example 1, at a concentration of 11.8 mg/ml, is placed in a 100 ml flask. The solution is shaken in a thermostat bath set at 4° C. 0.39 g of benzydamine base is diluted with 10 ml of tert-butanol and the solution is slowly added drop by drop to the hyaluronic acid solution: a white precipitate is formed which disappears within a few hours. The container used to weigh the benzydamine is washed with two 5 ml aliquots of tert-butanol which are then added to the hyaluronic acid solution. Some hours later, when there is no longer any suspended precipitate in the hyaluronic acid solution, 92.6 mg of $Ca(OH)_2$ are added and the mixture is shaken for several hours. The salification reaction is considered to be complete when there is no more precipitate in the solution.

At this point the solution is filtered through a Gooch G4 filter, subdivided into yellow glass bottles and freeze-dried. The neutral salt, partially salified (50%) with benzydamine and partially salified (50%) with calcium, is thus obtained.

The benzydamine used as starting product can be prepared as described in Example 4.

Example 8

250 ml of an aqueous solution of hyaluronic acid, prepared as in Example 2, at a concentration of 3.78 mg/ml, is placed in a 500 ml flask. The solution is shaken in a thermostat bath set at 4° C. 0.39 g of benzydamine base is diluted with 10 ml of tert-butanol and the solution is slowly added drop by drop to the hyaluronic acid solution. A white precipitate is formed which disappears within a few hours. The container used to weigh the benzydamine is washed with two 10 ml aliquots of tert-butanol which are then added to the hyaluronic acid solution. Some hours later, when there is no longer any suspended precipitate in the hyaluronic acid solution, 1.25 ml of NaOH 1N are added and the mixture is shaken for another 30 minutes.

At this point the solution is filtered through a Gooch G4 filter, subdivided into yellow glass bottles and freeze-dried. The neutral salt, partially salified (50%) with benzydamine and partially salified (50%) with calcium, is thus obtained.

The benzydamine used as starting product can be prepared as described in Example 4.

Example 9

250 ml of an aqueous solution of hyaluronic acid, prepared as in Example 2, at a concentration of 3.78 mg/ml, is placed in a 500 ml flask. The solution is shaken in a thermostat bath set at 4° C. 0.39 g of benzydamine base is diluted with 10 ml of tert-butanol and the solution is slowly added drop by drop to the hyaluronic acid solution: a white precipitate is formed which disappears within a few hours. The container used to weigh the benzydamine is washed with two 5 ml aliquots of tert-butanol which are then added to hyaluronic acid solution. A few hours later, when there is no longer any suspended precipitate in the solution, 92.6 mg of $Ca(OH)_2$ is added and the mixture is shaken for a few hours. The salification reaction is considered to be complete when there is no more precipitate in the solution.

At this point the solution is filtered through a Gooch G4 filter, subdivided into yellow glass bottles and freeze-dried. The neutral salt, partially salified (50%) with benzydamine and partially salified (50%) with calcium is thus obtained.

The benzydamine used as starting product can be prepared as described in Example 4.

Example 10

400 ml of an aqueous solution of hyaluronic acid, prepared as in Example 3, at a concentration of 2.36 mg/ml, is placed in a 500 ml flask. The solution is shaken in a thermostat bath set at 4° C. 0.39 g of benzydamine base is diluted with 10 ml of tert-butanol and the solution is slowly added drop by drop to the hyaluronic acid solution. A white precipitate is formed which disappears within a few hours. The container used to weigh the benzydamine is washed with two 10 ml aliquots of tert-butanol which are then added to the hyaluronic acid solution. Some hours later, when there is no more suspended precipitate in the solution, 125 ml of NaOH is added and the mixture is shaken for another 30 minutes.

At this point the solution is filtered through a Gooch G4 filter, subdivided into yellow glass bottles and freeze-dried. The neutral salt, partially salified (50%) with benzydamine and partially salified (50%) with sodium is thus obtained.

The benzydamine used as starting product can be prepared as described in Example 4.

Example 11

400 ml of an aqueous solution of hyaluronic acid, prepared as in Example 3, at a concentration of 2.36 mg/ml is placed in a 500 ml flask. The solution is shaken in a thermostat bath set at 4° C. 0.39 g of benzydamine base is diluted with 10 ml of tert-butanol and the solution is slowly added drop by drop to the hyaluronic acid solution. A white precipitate is formed which disappears within a few hours. The container used to weigh the benzydamine is washed with two 5 ml aliquots of tert-butanol which are then added to the hyaluronic acid solution. Some hours later, when there is no more suspended precipitate in the solution, 92.6 mg of $Ca(OH)_2$ is added and the mixture is shaken for another few hours. The salification reaction is considered to be complete when there is no longer any precipitate in the solution.

At this point the solution is filtered through a Gooch G4 filter, subdivided into yellow glass bottles and freeze-dried. The neutral salt, partially salified (50%) with benzydamine and partially salified (50%) with calcium is thus obtained.

The benzydamine used as starting product can be prepared as described in Example 4.

Example 12

80 ml of an aqueous solution of hyaluronic acid, prepared as in Example 1, at a concentration of 11.8 mg/ml, is placed in a 100 ml flask. The solution is shaken in a thermostat bath set at 4° C. 0.72 g of bupivacaine base is added in solid form to the solution and shaken for several hour. The salification reaction is considered to be complete when there is no longer any suspended precipitate in the solution.

At this point the solution is filtered through a Gooch G4 filter, subdivided into yellow glass bottles and freeze-dried. The stoichiometrically neutral salt of hyaluronic acid with bupivacaine is thus obtained.

The bupivacaine used as starting product can be prepared as follows: 3.0 g of bupivacaine hydrochloride is solubilized in water at a concentration of 25 mg/ml. An equimolar quantity of NaOH 1N is added slowly, plus 5% excess, so as to bring the aqueous solution to a pH of between 10 and 11.

In these conditions the bupivacaine base is released and separates from the water as a precipitate. The precipitate is filtered through a Gooch G4 filter, washed several times with water, then vacuum-dried. The product thus obtained is tested for purity by assessing its fusion point (107°–108°) and TLC (eluent:ethyl acetate/methanol 70:30; Rf=0.79).

Example 13

80 ml of an aqueous solution of hyaluronic acid, prepared as in Example 1, at a concentration of 11.8 mg/ml, is placed in a 100 ml flask. The solution is shaken in a thermostat bath set at 4° C.

0.54 g of bupivacaine base is added in solid form to the solution and shaken. Several hours later, when there is no longer any suspended precipitate in the solution, 0.62 ml of NaOH 1N is slowly added and shaken for another 30 minutes. At this point the solution is filtered through a Gooch G4 filter, subdivided into yellow glass bottles and freeze-dried. The neutral salt, partially salified (75%) with bupivacaine and partially salified (25%) with sodium, is thus obtained.

The bupivacaine used as starting product can be prepared as described in Example 12.

Example 14

80 ml of an aqueous solution of hyaluronic acid, prepared as in Example 1, at a concentration of 11.8 mg/ml, is placed in a 100 ml flask. The solution is shaken in a thermostat bath set at 4° C.

0.36 g of bupivacaine base is added in solid form to the solution and shaken. Several hours later, when there is no longer any suspended precipitate in the solution, 1.25 ml of NaOH 1N are slowly added and shaken for another 30 minutes.

At this point the solution is filtered through a Gooch G4 filter, subdivided into yellow glass bottles and freeze-dried. The neutral salt, partially salified (50%) with bupivacaine and partially salified (50%) with sodium, is thus obtained.

The bupivacaine used as staring product can be prepared as described in Example 12.

Example 15

80 ml of an aqueous solution of hyaluronic acid, prepared as in Example 1, at a concentration of 11.8 mg/ml, is placed in a 100 ml flask. The solution is shaken in a thermostat bath set at 4° C. 0.36 q of bupivacaine base is added in solid form to the solution and shaken. Several hours later, when there is no longer any suspended precipitate in the solution, 46.3 mg of $Ca(OH)_2$ 1N are added and shaken. The salification reaction is considered to be complete when there is no longer any precipitate in the solution.

At this point the solution is filtered through a Gooch G4 filter, subdivided into yellow glass bottles and freeze-dried. The neutral salt, partially salified (50%) with bupivacaine and partially salified (50%) with calcium, is thus obtained.

The bupivacaine used as starling product can be prepared as described in Example 12.

Example 16

250 ml of an aqueous solution of hyaluronic acid, prepared as in Example 2, at a concentration of 3.78 mg/ml is placed in a 500 ml flask. The solution is shaken in a thermostat bath set at 4° C. 0.72 g of bupivacaine base is added in solid form to the solution and shaken for several hours. The salification reaction is considered to be complete when there is no longer any suspended precipitate in the solution.

At this point the solution is filtered through a Gooch G4 filter, subdivided into yellow glass bottles and freeze-dried. The stoichiometrically neutral salt of hyaluronic acid with bupivacaine is thus obtained.

The bupivacaine used as starting product can be prepared as described in Example 12.

Example 17

250 ml of an aqueous solution of hyaluronic acid, prepared as in Example 2, at a concentration of 3.78 mg/ml, is placed in a 500 ml flask. The solution is shaken in a thermostat bath set at 4° C. 0.54 g of bupivacaine base is added in solid form to the solution and shaken. Several hours later, when there is no longer any suspended precipitate in the solution, 0.62 ml of NaOH 1N are slowly added and shaken for another 30 minutes.

At this point the solution is filtered through a Gooch 4 filter, subdivided into yellow glass bottles and freeze-dried. The neutral salt partially salified (75%) with bupivacaine and partially salified (25%) with sodium is thus obtained.

The bupivacaine used as starting product can be prepared as described in Example 12.

Example 18

250 ml of an aqueous solution of hyaluronic acid, prepared as in Example 2, at a concentration of 3.78 mg/ml, is placed in a 500 ml flask. The solution is shaken in a thermostat bath set at 4° C. 0.36 g of bupivacaine base is added in solid form to the solution and shaken. Several hours later, when there is no longer any suspended precipitate in the solution, 1.25 ml of NaOH 1N is slowly added and shaken for another 30 minutes.

At this point the solution is filtered through a Gooch G4 filter, subdivided into yellow glass bottles and freeze-dried. The neutral salt partially salified (50%) with bupivacaine and partially salified (50%) with sodium is thus obtained.

The bupivacaine used as starting product can be prepared as described in Example 12.

Example 19

250 ml of an aqueous solution of hyaluronic acid, prepared as in Example 2, at a concentration of 3.78 mg/ml, is placed in a 500 ml flask. The solution is shaken in a thermostat bath set at 4° C. 0.36 g of bupivacaine base is added in solid form to the solution and shaken. Several hours later, when there is no longer any suspended precipitate in the solution, 46.3 mg of $Ca(OH)_2$ is added and shaken. The salification reaction is considered to be complete when there is no longer any suspended precipitate in the solution.

At this point the solution is filtered through a Gooch G4 filter, subdivided into yellow glass bottles and freeze-dried. The neutral salt partially salified (50%) with bupivacaine and partially salified (50%) with calcium is thus obtained.

The bupivacaine used as starting product can be prepared as described in Example 12.

Example 20

400 ml of an aqueous solution of hyaluronic acid, prepared as in Example 3, at a concentration of 2.36 mg/ml, is placed in a 500 ml flask. The solution is shaken in a thermostat bath set at 4° C. 0.72 g of bupivacaine base is added in solid form to the solution and shaken for several hours. The salification reaction is considered to be complete when there is no longer any suspended precipitate in the solution.

At this point the solution is filtered through a Gooch G4 filter, subdivided into yellow glass bottles and freeze-dried. The stoichiometrically neutral salt of hyaluronic acid with bupivacaine is thus obtained.

The bupivacaine used as starting product can be prepared as described in Example 12.

Example 21

400 ml of an aqueous solution of hyaluronic acid, prepared as in Example 3, at a concentration of 2.36 mg/ml, is placed in a 500 ml flask. The solution is shaken in a thermostat bath set a 4° C. 0.54 g of bupivacaine base is added in solid form to the solution and shaken. Several hours later, when there is no longer any suspended precipitate in the solution, 0.62 ml of NaOH 1N are slowly added and shaken for another 30 minutes.

At this point the solution is filtered through a Gooch G4 filter, subdivided into yellow glass bottles and freeze-dried. The neutral salt partially salified (75%) with bupivacaine and partial salified (25%) with sodium is thus obtained.

The bupivacaine used as starting product can be prepared as described in Example 12.

Example 22

400 ml of an aqueous solution of hyaluronic acid, prepared as in Example 3, at a concentration of 2.36 mg/ml, is placed in a 500 ml flask. The solution is shaken in a thermostat bath set at 4° C. 0.36 g of bupivacaine base is added in solid form to the solution and shaken. Several hours later, when there is no longer any suspended precipitate in the solution, 125 ml of NaOH 1N are slowly added and shaken for another 30 minutes.

At this point the solution is filtered through a Gooch G4 filter, subdivided into yellow glass bottles and freeze-dried. The neutral salt partially salified (50%) with bupivacaine and partially salified (50%) with sodium is thus obtained.

The bupivacaine used as starting product can be prepared as described in Example 12.

Example 23

400 ml of an aqueous solution of hyaluronic acid, prepared as in Example 3, at a concentration of 2.36 mg/ml, is placed in a 500 ml flask. The solution is shaken in a thermostat bath set at 4° C. 0.36 g of bupivacaine base is added in solid form to the solution and shaken. Several hours later, when there is no longer any suspended precipitate in the solution, 46.3 mg of $Ca(OH)_2$ is slowly added and shaken. The salification reaction is considered to be complete when there is no longer any precipitate in the solution.

At this point the solution is filtered through a Gooch G4 filter, subdivided into yellow glass bottles and freeze-dried. The neutral salt partially salified (50%) with bupivacaine and partially salified (50%) with calcium is thus obtained.

The bupivacaine used as staring product can be prepared as described in Example 12

Example 24

80 ml of an aqueous solution of hyaluronic acid, prepared as in Example 1 at a concentration of 11.8 mg/ml, is placed in a 100 ml flask. The solution is shaken in a thermostat bath set at 4° C. 0.59 g of lidocaine base is added in solid form to the solution and shaken for several hours. The salification reaction is considered to be complete when there is no longer any suspended precipitate in the solution.

At this point the solution is filtered through a Gooch G4 filter, subdivided into yellow glass bottles and freeze-dried. The stoichiometrically neutral salt of hyaluronic acid with lidocaine is thus obtained.

The lidocaine used as starting product can be prepared as follows; 3.0 g of lidocaine hydrochloride is solubilized in water to a concentration of 25 mg/ml. An equimolar quantity of NaOH is slowly added, plus an excess of 5%, so as to give the aqueous solution a pH of between 10 and 11. In these conditions, lidocaine base is released and this separates from the water in the form of a precipitate. The precipitate is filtered through a Gooch G4 filter, washed several times with water and then vacuum-dried. The purity of the product thus obtained is tested by means of its fusion point (68°–69° C.) and TLC (eluent: ethyl acetate/methanol 70:30;Rf=0.81)

Example 25

80 ml of an aqueous solution of hyaluronic acid, prepared as in Example 1, at a concentration of 11.8 mg/ml, is placed in a 100 ml flask. The solution is shaken in a thermostat bath set at 40° C. 0.44 g of lidocaine base is added in solid form to the solution and shaken. Several hours later, when there is no longer any suspended precipitate in the solution, 0.62 ml of NaOH 1N are slowly added and shaken for another 30 minutes.

At this point the solution is filtered through a Gooch G4 filter, subdivided into yellow glass bottles and freeze-dried. The neutral salt partially salified (75%) with lidocaine and partially salified (50%) with sodium is thus obtained.

The lidocaine used as starting product can be prepared as described in Example 24.

Example 26

80 ml of an aqueous solution of hyaluronic acid, prepared as in Example 3, at a concentration of 11.8 mg/ml, is placed in a 100 ml flask. The solution is shaken in a thermostat bath set at 4° C. 0.29 g of lidocaine base is added in solid form to the solution and shaken. Several hours later, when there is no longer any suspended precipitate in the solution, 1.25 ml of NaOH 1N is slowly added and shaken for another 30 minutes.

At this point the solution is filtered through a Gooch G4 filter, subdivided into yellow glass bottles and freeze-dried. The neutral salt partially salified (50%) with lidocaine and partially salified (50%) with sodium is thus obtained.

The lidocaine used as starting product can be prepared as described in Example 24.

Example 27

80 ml of an aqueous solution of hyaluronic acid, prepared as in Example 1, at a concentration of 11.8 mg/ml, is placed in a 500 ml flask. The solution is shaken in a thermostat bath set at 4° C. 0.44 g of lidocaine base is added in solid form to the solution and shaken. Several hours later, when there is no longer any suspended precipitate in the solution, 23 mg of $Ca(OH)_2$ is added and shaken. The salification reaction is considered to be complete when there is no longer any precipitate in the solution.

At this point the solution is filtered through a Gooch G4 filter, subdivided into yellow glass bottles and freeze-dried. The neutral salt partially salified (75%) with lidocaine and partially salified (25%) salified with calcium is thus obtained.

The lidocaine used as starting product can be prepared as described in Example 24.

Example 28

80 ml of an aqueous solution of hyaluronic acid, prepared as in Example 1, at a concentration of 11.8 mg/ml, is placed in a 100 ml flask. The solution is shaken in a thermostat bath set at 4° C. 0.29 g of lidocaine base is added in solid form to the solution and shaken. Several hours later, when there is no longer any suspended precipitate in the solution, 46.3 mg of $Ca(OH)_2$ is slowly added and shaken. The salification reaction is considered to be complete when there is no longer any precipitate in the solution.

At this point the solution is filtered through a Gooch G4 filter, subdivided into yellow glass bottles and freeze-dried. The neutral salt partially salified (50%) with lidocaine and partially salified (50%) with calcium is thus obtained The lidocaine used as staring product can be prepared as described in Example 24.

Example 29

80 ml of an aqueous solution of hyaluronic acid, prepared as in Example 1, at a concentration of 11.8 mg/ml, is placed in a 100 ml flask. The solution is shaken in a thermostat bath set at 4° C. 0.29 g of lidocaine base is added in solid form to the solution and shaken. Several hours later, when there is no longer any suspended precipitate in the solution, 36.5 mg of $Mg(OH)_2$ is added and shaken. The salification reaction is considered to be complete when there is no longer any precipitate in the solution.

At this point the solution is filtered through a Gooch G4 filter, subdivided into yellow glass bottles and freeze-dried. The neutral salt partially salified (50%) with lidocaine and partially salified (50%) with magnesium is thus obtained.

The lidocaine used as starting product can be prepared as described in Example 24.

Example 30

80 ml of an aqueous solution of hyaluronic acid, prepared as in Example 1, at a concentration of 11.8 mg/ml is placed in a 100 ml flask. The solution is shaken in a thermostat bath set at 4° C. 0.29 g of lidocaine base is added in solid form to the solution and shaken. Several hours later, when there is no longer any suspended precipitate in the solution, 1.25 ml of LiOH 1N is slowly added and shaken for another 30 minutes.

At this point the solution is filtered through a Gooch G4 filter, subdivided into yellow glass bottles and freeze-dried. The neutral salt partially salified (50%) with lidocaine and partially salified (50%) with lithium is thus obtained.

The lidocaine used as staring product can be prepared as described in Example 24.

Example 31

80 ml of an aqueous solution of hyaluronic acid, prepared as in Example 1, at a concentration of 11.8 mg/ml, is placed in a 100 ml flask. The solution is shaken in a thermostat bath set at 4° C. 0.29 g of lidocaine base is added in solid form to the solution and shaken. Several hours later, when there is no longer any suspended precipitate in the solution, 1.25 ml of KOH 1N is added and shaken for another 30 minutes.

At this point the solution is filtered through a Gooch G4 filter, subdivided into yellow glass bottles and freeze-dried. The neutral salt partially salified (50%) with lidocaine and partially salified (50%) with potassium is thus obtained.

The lidocaine used as starting product can be prepared as described in Example 24.

Example 32

80 ml of an aqueous solution of hyaluronic acid, prepared as in Example 1, at a concentration of 11.8 mg/ml is placed in a 100 ml flask. The solution is shaken in a thermostat bath set at 4° C. 0.69 G of benzydamine base are diluted with 10 ml of tert-butanol and the solution is slowly added drop by drop to the hyaluronic acid solution: a white precipitate is formed which disappears within a few hours. The container used to weigh the benzydamine is washed with two 5 ml aliquots of tert-butanol which are then added to the hyaluronic acid solution. A few hours later, when there is no more suspended precipitate in the solution, 0.25 ml of NaOH 1N is added and shaken for another 30 minutes.

At this point the solution is filtered through a Gooch G4 filer, subdivided into yellow glass bottles and freeze-dried. The neutral salt, partially salified (90%) with benzydamine and partially salified (10%) with sodium is thus obtained.

The benzydamine to be used as staring product can be prepared as described in Example 4.

Example 33

80 ml of an aqueous solution of hyaluronic acid, prepared as in Example 1, at a concentration of 11.8 mg/ml is placed in a 100 ml flask. The solution is shaken in a thermostat bath set at 4° C. 0.19 g of benzydamine base are diluted with 10 ml of tert-butanol and the solution is slowly added drop by drop to the hyaluronic acid solution: a white precipitate is formed which disappears within a few hours. The container used to weigh the benzydamine is washed with two 5 ml aliquots of tert-butanol which are then added to the hyaluronic acid solution. A few hours later, when there is no more suspended precipitate in the solution, 1.87 ml of NaOH 1N is added and shaken for another 30 minutes.

At this point the solution is filtered through a Gooch G4 filter, subdivided into yellow glass bottles and freeze-dried. The neutral salt, partially salified (25%) with benzydamine and partially salified (75%) with sodium is thus obtained.

The benzydamine to be used as starting product can be prepared as described in Example 4.

Example 34

80 ml of an aqueous solution of hyaluronic acid, prepared as in Example 1, at a concentration of 11.8 mg/ml is placed in a 100 ml flask. The solution is shaken in a thermostat bath set at 4° C. 0.08 g of benzydamine base are diluted with 10 ml of tert-butanol and the solution is slowly added drop by drop to the hyaluronic acid solution: a white precipitate is formed which disappears within a few hours. The container used to weigh the benzydamine is washed with two 5 ml aliquots of tert-butanol which are then added to the hyaluronic acid solution. A few hours later, when there is no more suspended precipitate in the solution, 2.24 ml of NaOH 1N is added and shaken for another 30 minutes.

At this point the solution is filtered through a Gooch G4 filter, subdivided into yellow glass bottles and freeze-dried. The neutral salt, partially salified (10%) with benzydamine and partially salified (90%) with sodium is thus obtained.

The benzydamine to be used as starting product can be prepared as described in Example 4.

Example 35

80 ml of an aqueous solution of hyaluronic acid, prepared as in Example 1, at a concentration of 11.8 mg/ml is placed in a 100 ml flask. The solution is shaken in a thermostat bath set at 4° C. 0.18 g of bupivacaine base in solid form is added to the solution and shaken. Several hours later, when there is no longer any suspended precipitate in the solution, 1.87 ml of NaOH 1N is slowly added and shaken for another 30 minutes. At this point the solution is filtered through a Gooch G4 filter, subdivided into yellow glass bottles and freeze-dried. The neutral salt, partially salified (25%) with bupivacaine and partially salified (75%) with sodium, is thus obtained.

The bupivacaine used as starting product can be prepared as described in Example 12.

PHARMACEUTICAL PREPARATIONS

| Preparation 1: | |
|---|---|
| Preparation of a mouthwash containing Benzydamine hyaluronate (75%) 100 ml of solution contain: | |
| Benzydamine hyaluronate (equal to 134.4 mg of benzydamine base) Excipients | 357 mg |
| Glycerol | 5000 mg |
| ethyl alcohol 95° | 7926 mg |
| Saccharine | 30 mg |
| Methyl p-hydroxybenzoate | 180 mg |
| Propyl p-hydroxybenzoate | 20 mg |
| Peppermint flavouring | 42.62 mg |
| Quinoline yellow colouring (E104) | 0.87 mg |
| Blue patent V colouring (E131) | 0.14 mg |
| Purified water q.s. to | 100 ml |

| Preparation 2: | |
|---|---|
| Preparation of a spray containing Benzydamine hyaluronate (75%) 100 ml of solution contain: | |
| Benzydamine hyaluronate (equal to 134.4 mg of benzydamine base) Excipients | = 357 mg |
| Glycerol | 5000 mg |
| Ethyl alcohol 95° | 7926 mg |
| Saccharine | 30 mg |
| Methyl p-hydroxybenzoate | 180 mg |
| Propyl p-hydroxybenzoate | 20 mg |
| Peppermint flavouring | 42.62 mg |
| Purified water q.s. to | 100 ml |

| Preparation 3: | |
|---|---|
| Preparation of a proctological cream containing Benzydamine hyaluronate (75%) 100 ml of cream contain: | |
| Benzydamine hyaluronate (equal to 448 mg of benzydamine base) Excipients | 1190 mg |
| Vaseline | 8000 mg |
| Vaseline oil | 4000 mg |
| Lanolin | 12000 mg |
| Polysorbate 80 | 5000 mg |
| Propylene glycol | 6000 mg |
| Methyl p-hydroxybenzoate | 93.5 mg |
| Propyl p-hydroxybenzoate | 34 mg |
| Lavender essence | 42 mg |
| Purified water q.s. to | 100 ml |

| -continued | |
|---|---|
| Preparation 4: | |
| Preparation of a gynaecological solution containing Benzydamine hyaluronate (75%) 100 ml of solution contain: | |
| Benzydamine hyaluronate Excipients: | 238 mg |
| Trimethylacetylammonium-p-toluene sulfonate | 100 mg |
| Red rose scent | 0.1 ml |
| Purified water q.s. to | 100 ml |

The invention being thus described, it is clear that these methods can be modified in various ways. Said modifications are not to be considered as divergences from the spirit and purposes of the invention, and any modification which would be apparent to an expert in the field comes within the scope of the following claims.

What is claimed is:

1. A medicament for topical administration comprising a stoichiometrically neutral salt of hyaluronic acid with benzydamine or bupivacaine, in which at least 50% of the carboxy groups of the hyaluronic acid are salified with the benzydamine or bupivacaine and the remaining carboxy groups are salified with an alkaline or alkaline earth metal, wherein the hyaluronic acid has a molecular weight in the range of 50–350 kDa or 500–730 kDa or 750–1,200 kDa.

2. A medicament for topical administration according to claim 1, wherein the alkaline metal is sodium.

3. A medicament for topical administration according to claim 1, wherein the alkaline earth metal is calcium.

4. A medicament for topical administration according to any one of claims 1–3, wherein the carboxy groups of hyaluronic acid are salified with benzydamine or bupivacaine in the range between 70 and 100%.

5. A medicament for topical administration according to claim 4, wherein the carboxy groups of hyaluronic acid are salified with benzydamine in a percentage of about 75%.

6. A medicament for topical administration according to claim 4, wherein the carboxy groups of hyaluronic acid are salified with bupivacaine in a percentage of about 100%.

7. A medicament for topical administration according to claim 5, wherein the hyaluronic acid has a molecular weight in the range of 50–350 kDa.

8. A medicament for topical administration according to claim 6, wherein the hyaluronic acid has a molecular weight in the range of 500–730 kDa.

9. A medicament as defined in claim 1 for use in ophthalmology.

10. A method for the treatment of inflammatory processes in the mouth or primary airways, including rhinitis, mucositis caused by radiotherapy or chemotherapy, by intubation during surgery or for diagnostic purposes, in periodontal or gingival conditions, in inflammatory processes in the auditory canal, in conjunctivitis of various origin, in vulvovaginitis, urethritis, or for proctological applications which comprises administering an effective amount of a medicament according to claim 1.

11. A medicament as defined in claim 1, for use as an anesthetic.

12. A medicament according, claim 1 which is in the form of collirium, mouth wash, spray, cream or vaginal solution.

* * * * *